US012642703B2

(12) United States Patent
Seymour

(10) Patent No.: US 12,642,703 B2
(45) Date of Patent: Jun. 2, 2026

(54) EYE SHIELD

(71) Applicant: Laura Seymour, Houston, TX (US)

(72) Inventor: Laura Seymour, Houston, TX (US)

( * ) Notice: Subject to any disclaimer, the term of this patent is extended or adjusted under 35 U.S.C. 154(b) by 0 days.

(21) Appl. No.: 18/907,035

(22) Filed: Oct. 4, 2024

(65) Prior Publication Data

US 2026/0096930 A1     Apr. 9, 2026

(51) Int. Cl.
*A61F 9/04* (2006.01)

(52) U.S. Cl.
CPC .................................... *A61F 9/045* (2013.01)

(58) Field of Classification Search
CPC .............. G02C 7/16; G02C 5/00–005; G02C 3/00–04; A61F 9/04; A61F 9/045; A61F 13/12; A61F 13/124
See application file for complete search history.

(56) References Cited

U.S. PATENT DOCUMENTS

| | | | | |
|---|---|---|---|---|
| 542,015 A | * | 7/1895 | Goodman | A61F 9/045 2/13 |
| 1,080,893 A | * | 12/1913 | Collier | G02C 7/16 2/432 |
| 1,706,667 A | * | 3/1929 | Haustein | A61F 9/045 2/431 |
| 1,918,264 A | * | 7/1933 | Harpster | G02C 7/16 2/12 |
| 1,930,972 A | * | 10/1933 | Griswold | A61F 9/04 2/11 |
| 2,460,373 A | * | 2/1949 | Waldman | G02C 7/16 2/432 |
| 3,441,341 A | * | 4/1969 | Dunn | G02C 5/005 351/63 |
| 4,955,709 A | * | 9/1990 | Smith | G02C 7/16 351/44 |

FOREIGN PATENT DOCUMENTS

WO      WO-2019096972 A1 *  5/2019  .............. G02C 1/00

* cited by examiner

*Primary Examiner* — Michelle J Lee

(57) ABSTRACT

An eye shield device for covering, protecting, or obscuring an eye of a wearer of the eye shield device. The eye shield device may be worn in multiple configurations including a headband and over the ear versions. The eye shield device includes a cantilevered arm structure to project forward the mounting arm or portion for an eye shield. Some embodiments may include a cross-member arm to hold the eye shield or the eye shield may directly connect or project from a proximal end of the cantilevered arm. Some embodiments may include the eye shield device comprised of rigid, yet flexible, materials, such as polymer plastics, metals, alloys, or combinations of the same. Other embodiments may include a detachable eye shield to allow the wearer to customize their appearance. Other embodiments may include modular fixtures to allow the wearer to change the length of projection of the arm, crossmember arm, or headband or earpiece.

6 Claims, 3 Drawing Sheets

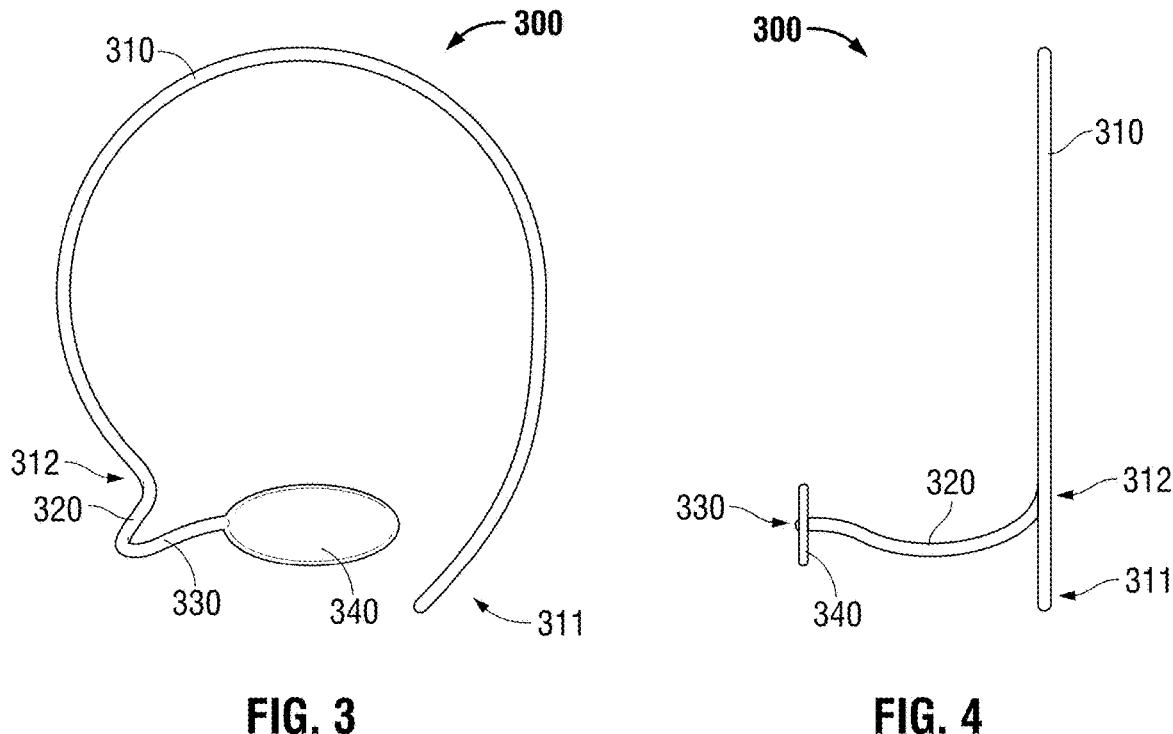
FIG. 3          FIG. 4
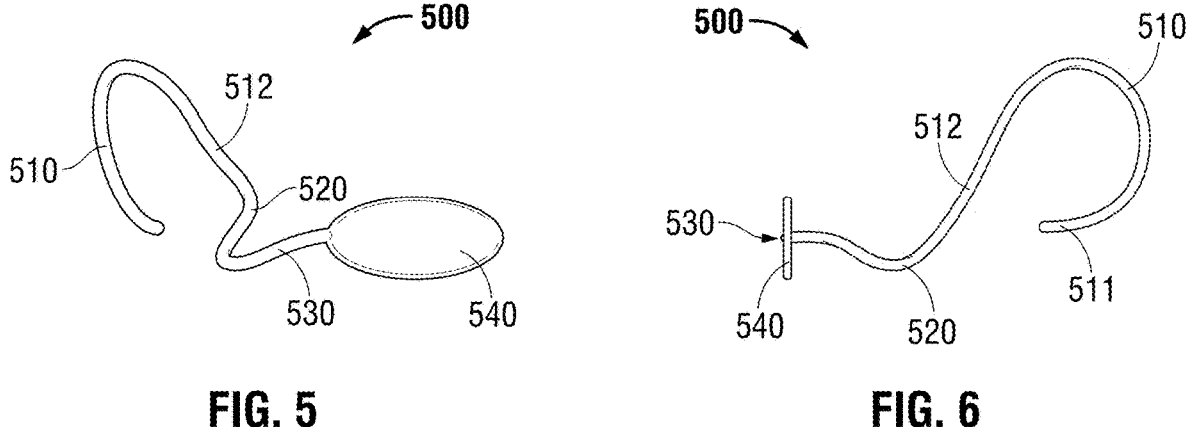
FIG. 5          FIG. 6

EYE SHIELD

STATEMENT REGARDING FEDERALLY SPONSORED RESEARCH

Not applicable.

BACKGROUND

Many people require the use of corrective lenses, such as glasses or contacts, other people may instead choose to undergo elective or necessary surgery to repair or amend some of their eyesight. Still other people may have deficient or insufficient sight capabilities and elect to use an eyepatch or darkened glass lenses to obscure one or more of their eyes. Typical eyepatches, while useful in achieving the obscuration of the wearer's eye(s), can be uncomfortable by applying pressure directly on the wearer's face, check, forehead, or eye. Additionally, eyepatches typically require that the strap or band impress or indent across the wearer's skin, face, and/or hair.

There is a long felt need for an eye shield that allows for customizability, comfortable all day wear, and does not leave an impression or indentation on the wearer's skin, face, or hair as is common with typical eye patches.

SUMMARY

The present invention relates to an eye shield affixed to a cantilevered arm that extends from a headband that can be worn over the crown of the wearer's head and in front of or behind the wearer's ears, whichever the wearer may find most comfortable or to suit their stylistic choices. Thus, allowing for minimal facial impact or indentation from wearing the head banded eye shield. Other embodiments of the present invention relate to an eye shield affixed to a cantilevered arm that extends from an over-the-ear clip allowing for minimal facial impact or indentation from wearing the eye shield. Such embodiments also minimize the contact or impact with the wearer's hair style or may provide an alternative to wearers that would prefer not to wear an over the crown headband eye shield device.

Some embodiments allow for the eye shield to be removably connected to the cantilevered arm to allow for the wearer to interchange different eye shield covers to change or modified the size of the eye shield being worn, colors, designs, or shapes.

Some embodiments include an eye shield device comprising a headband member, wherein the headband member comprises a curved shape having a distal end and a proximal end; a projecting member, wherein said projecting member projects from said proximal end of said headband member; a cross member, wherein said cross member extends substantially perpendicular from said projecting member and aligns substantially parallel with said headband member; and an eye shield. Some embodiments may include a headband made of a rigid and flexible material. Some embodiments may include a projecting member that is made of a rigid and flexible material. Some embodiments may include a cross member that is made of a rigid and flexible material. Some embodiments may include a cross member further comprising a mating connector for receiving said eye shield, wherein said eye shield has a mating connector for fixedly engaging said eye shield and said cross member. Some embodiments may include a projecting member and a cross member that are a unitary piece of material. Some embodiments may include a headband, projecting member, cross member, and eye shield that are a unitary piece of material.

Other embodiments may include an eye shield device comprising: an earpiece member, wherein the earpiece member comprises a curved shape having a distal end and a proximal end; a projecting member, wherein said projecting member projects from said proximal end of said earpiece member; a cross member, wherein said cross member extends substantially perpendicular from said projecting member and aligns substantially perpendicular with said earpiece member; and an eye shield. Some embodiments may include an earpiece made of a rigid and flexible material. Some embodiments may include a projecting member made of a rigid and flexible material. Some embodiments may include a cross member made of a rigid and flexible material. Some embodiments may include a cross member comprising a mating connector for receiving said eye shield, wherein said eye shield has a mating connector for fixedly engaging said eye shield and said cross member. Some embodiments may include a projecting member and cross member that are a unitary piece of material. Some embodiments may include an earpiece, projecting member, cross member, and eye shield that are a unitary piece of material. Some embodiments may include an earpiece, projecting member, cross member, and eye shield that are comprised of a rigid and flexible material.

BRIEF DESCRIPTION OF THE DRAWINGS

FIG. 3 is a front view of an embodiment of the over-the-head variation of the present invention.

FIG. 4 is a side view of an embodiment of the over-the-head variation of the present invention.

FIG. 5 is a front view of an embodiment of the over-the-ear variation of the present invention.

FIG. 6 is a side view of an embodiment of the over-the-ear variation of the present invention.

DETAILED DESCRIPTION

Figure 1:
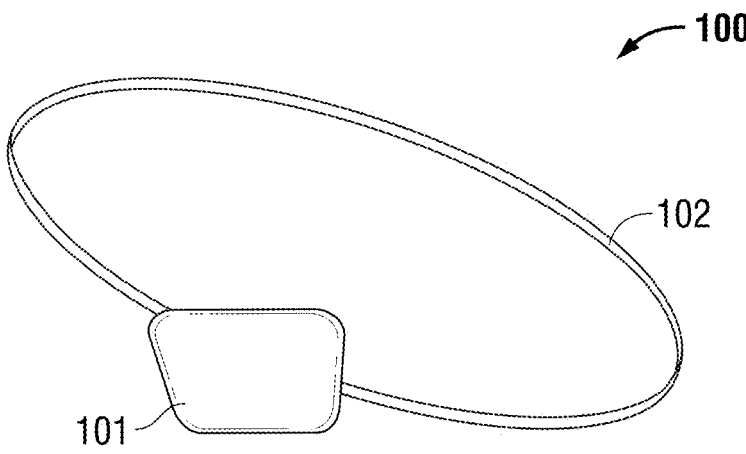
FIG. 1 is an isometric view of a typical eyepatch with a band or strap.

One or more illustrative embodiments incorporating the invention disclosed herein are presented below. The inventor has created a revolutionary and novel eye shield for use by persons intending to shield, protect, and/or obscure from view one or more of the wearer's eyes. Various illustrative embodiments include an over-the-head variation and an over-the-ear version. Each providing shielding, protection, or obscuring of one or more of the wearer's eyes.

In the following description, certain details are set forth such as specific quantities, sizes, etc. to provide a thorough understanding of the present embodiments disclosed herein. However, it will be evident to those of ordinary skill in the art that the present disclosure may be practiced without such specific details. In many cases, details concerning such considerations, and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing embodiments of the disclosure and are not intended to be limiting thereto. Drawings are not necessarily to scale, and arrangements of specific units in the drawings can vary.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless, or essentially meaningless, the definition should be taken from Webster's Dictionary 2024. Definitions and/or interpretations should not be incorporated from other patent applications, patents, or publications, related or not, unless specifically stated in this specification, or if the incorporation is necessary for maintaining validity.

While preferred embodiments have been shown, and described, modifications thereof can be made by one skilled in the art without departing from the scope or teaching herein. The embodiments described herein are exemplary only and are not limiting. Many variations and modifications of the system and apparatus are possible and will become apparent to those skilled in the art once the above disclosure is fully appreciated. For example, the relative dimensions of various parts, the materials from which the various parts are made, and other parameters can be varied.

Figure 2:
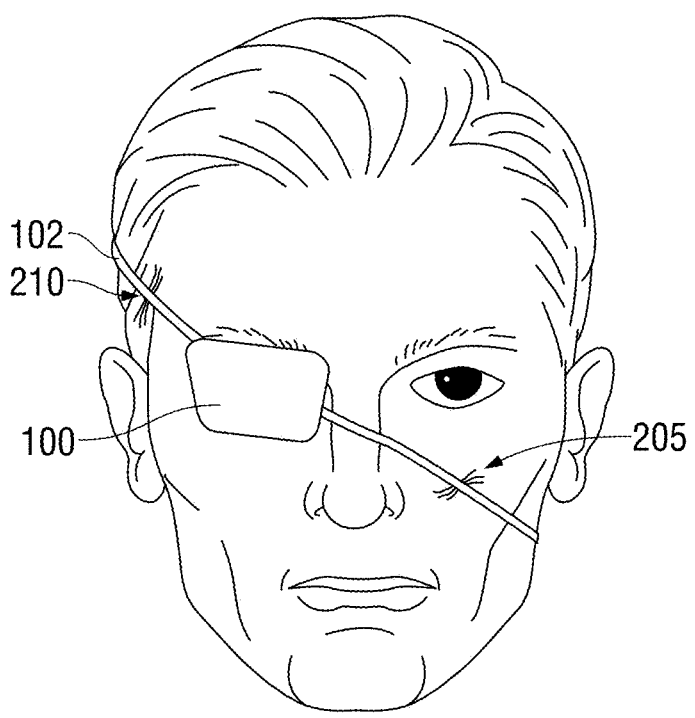
FIG. 2 is an isometric view of a typical eyepatch being worn by a wearer.

FIG. 1 shows a typical eyepatch device 100 that may be worn to protect, shield, or obscure a wearer's eye. The typical eyepatch device 100 includes a patch 101 and a band or strap 102, wherein the band or strap may include an adjustable length to accommodate different circumference heads or comfort levels of the wearer. FIG. 2 shows that even when adjustable, the typical eyepatch 100 still causes compression, indentation, and impression upon the wearer's skin, face, and/or hair as shown at points 205 and 210. Typical eyepatches can also interfere with other headgear, such as hats, caps, or glasses.

FIG. 3 depicts an embodiment of an eye shield device 300 comprising a headband 310, a cantilevered arm 320, a front arm 330, and an eye shield 340. It should be appreciated that the headband 301, cantilevered arm 320, front arm 330, and eye shield 340 are comprised of a rigid yet flexible material, such as various polymer plastics, biodegradable materials, metals, alloys, wood, bendable wire, or combinations thereof. The headband 310 is suitable for wearing as a typical headband to hold one's hair in place, typically with the ends extending down and behind the wearer's ears, including distal end 311 and proximal end 312. The cantilevered arm 320 extends substantially forward along the wearer's temple and side of the wearer's face to a distance substantially forward of the wearer's eye. The front arm 330 can be formed as a bend in a single piece of material comprising the cantilevered arm 320 or a two-piece composition. A multipart cantilevered arm and front arm system can allow for the wearer to use modular pieces to create a customized or unique style or look for their eye shield device. A benefit of the rigid yet flexible materials used in the composition allows for the wearer to position the eye shield 340 in a position best suited for their facial structure and eye positioning. It should be apparent that facial structures and eye positioning varies from person to person and even over an individual person's lifetime such that it would be advantageous to have a rigid yet flexible material to allow for positioning and repositioning of the eye shield 340 and arms 320 and 330. It should also be appreciated that the eye shield 340 may take numerous shapes or designs to accommodate a wearer's style, face or head size, or other aspects that the wearer may desire to accommodate.

FIG. 4 is a side view of an embodiment of the eye shield device 300. The side view demonstrates the headband 310 and the way the cantilevered arm 320 extends substantially forward of the headband 310 and along the wearer's temple and side of the wearer's face to a distance substantially forward of the wearer's eye. The front arm 330 (obscured in the side view by the depicted eye shield 340) can be formed as a bend in a single piece of material comprising the cantilevered arm 320 or a two-piece composition.

FIG. 5 is an alternative embodiment of an eye shield device 500. The eye shield device 500 is intended to be worn over and around a wearer's ear. The earpiece 510 is intended to rest on top of a wearer's ear with earpiece retaining arm 511 extending down and behind the wearer's ear. The cantilevered arm 520 extends substantially forward from the earpiece 510 and along the wearer's temple and side of the wearer's face to a distance substantially forward of the wearer's eye. The front arm 530 can be formed as a bend in a single piece of material comprising the cantilevered arm 520 or a two-piece composition. A multipart cantilevered arm and front arm system can allow for the wearer to use modular pieces to create a customized or unique style or look for their eye shield device. A benefit of the rigid yet flexible materials used in the composition allows for the wearer to position the eye shield 540 in a position best suited for their facial structure and eye positioning. It should be apparent that facial structures and eye positioning varies from person to person and even over an individual person's lifetime such that it would be advantageous to have a rigid yet flexible material to allow for positioning and repositioning of the eye shield 340 and arms 520 and 530. It should also be appreciated that the eye shield 540 may take numerous shapes or designs to accommodate a wearer's style, face or head size, or other aspects that the wearer may desire to accommodate. It should be appreciated that other embodiments of the earpiece may include a retaining clip in lieu of retaining arm 511. The retaining clip being capable of pinching a portion of the wearer's outer ear, e.g. the pinna, auricle, or cartilage. The retaining clip may include a form fitted custom molding specific to the wearer of the device. The retaining clip may include magnetic element to secure the earpiece to the wearer's ear and further include soft foam or other soft, hypoallergenic material on the interior of the clip for comfort of the wearer. Other versions of the retaining clip may include an ear bud style that fits into or rest on the outer portion of the ear canal. Other versions of the retaining clip may include an ear-piercing component, such as an industrial piercing, e.g. a barbell shaped jewelry extending through two pierced holes in the ear cartilage, for affixing the earpiece to the wearer's ear.

FIG. 6 is a side view of an embodiment of the eye shield device 500. The side view demonstrates the earpiece 510 and the way the cantilevered arm 520 extends substantially forward of the earpiece 510 and along the wearer's temple and side of the wearer's face to a distance substantially forward of the wearer's eye. The earpiece 510 is intended to rest on top of a wearer's ear with earpiece retaining arm 511 extending down and behind the wearer's ear. The front arm 530 (obscured in the side view by the depicted eye shield 540) can be formed as a bend in a single piece of material comprising the cantilevered arm 520 or a two-piece composition.

Figure 7:
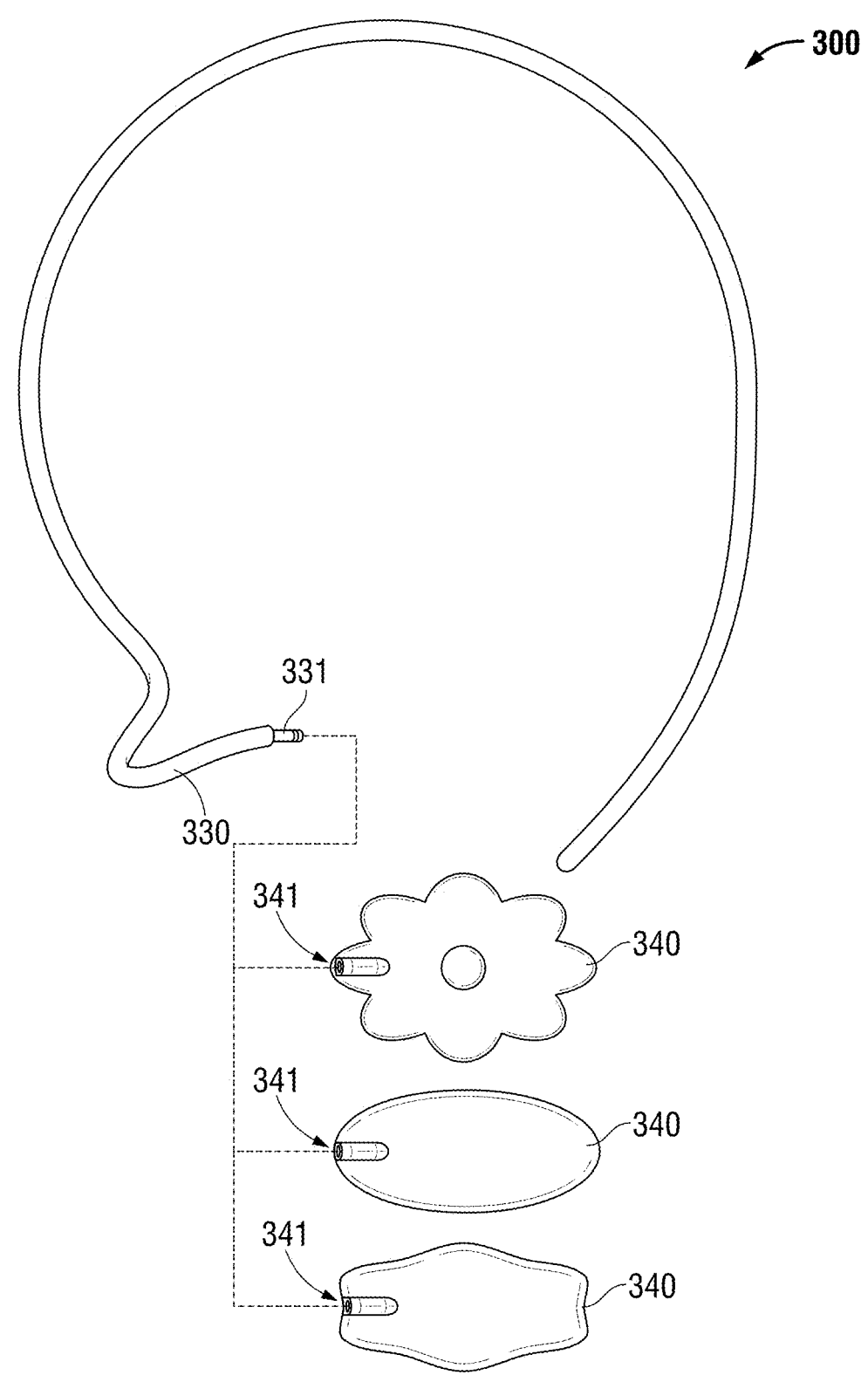
FIG. 7 is an exploded view of an embodiment of the present invention.

FIG. 7 is a front view of an alternative embodiment of the eye shield device 300 wherein the eye shield 340 is selectively removable to allow for modularity and alternative shapes, colors, and sizes to be implemented by the wearer. It should be appreciated that the front arm 330 includes a mating portion 331 that matches and allows for the selective removal and attachment of different eye shield 340. It should also be appreciated that the eye shield may include it own receiving or mating end 341. It should be appreciated that the engagement mechanism can be of different natures including magnets, press fit, sliding engagement, friction fit, pin(s), or similar as is known in the art of adjoining two or more pieces of material for a fixed connection capable of disengagement from the other piece.

While preferred embodiments have been shown and described, modifications thereof can be made by one skilled in the art without departing from the scope or teaching herein. The embodiments described herein are exemplary only and are not limiting. Many variations and modifications of the system and apparatus are possible and will become apparent to those skilled in the art once the above disclosure is fully appreciated. For example, the relative dimensions of various parts, the materials from which the various parts are made, and other parameters can be varied. Further, it should be appreciated that the disclosure and teachings of the several embodiments described herein may be used interchangeably to achieve different embodiments not explicitly depicted. Accordingly, it is intended that the following claims be interpreted to embrace all such variations and modifications.

The invention claimed is:

1. An eye shield device, for concealing a single eye of a user, comprising:

a headband member, wherein the headband member comprises a curved shape having a terminal distal end and a proximal end, wherein said headband member is configured to be worn superiorly over a crown portion of a head of the user such that said terminal distal end and proximal end are disposed behind the ears of the user;

a projecting member, comprising a distal end, wherein said projecting member is configured to project forward along a temple of the user and extend beyond the eye of the user, from said proximal end of said headband member;

a cross member, wherein said cross member extends perpendicularly from said distal end of said projecting member and aligns parallel with said headband member; wherein said headband member, projecting member, and cross member are a single piece of polymer plastic material, and an obscuring eye shield that is longer in a horizontal direction parallel to the cross member than a vertical direction.

2. The eye shield device of claim 1, wherein said cross member further comprises a mating connector for receiving said eye shield, wherein said eye shield has a mating connector for fixedly engaging said eye shield and said cross member.

3. The eye shield device of claim 2 wherein said eye shield aligns parallel to said headband member.

4. The eye shield device of claim 1, wherein said headband, said projecting member, said cross member, and said eye shield are a single piece of material.

5. The eye shield device of claim 4 wherein said eye shield aligns parallel to said headband member.

6. The eye shield device of claim 1 wherein said eye shield aligns parallel to said headband member.

* * * * *